United States Patent
Massey-Brooker et al.

(10) Patent No.: US 9,895,445 B2
(45) Date of Patent: *Feb. 20, 2018

(54) CONSUMER GOODS PRODUCT COMPRISING FUNCTIONALISED LIGNIN OLIGOMER

(71) Applicant: The Procter & Gamble Company, Cincinnati, OH (US)

(72) Inventors: Anju Deepali Massey-Brooker, Newcastle upon Tyne (GB); Mauro Vaccaro, Newcastle upon Tyne (GB); Stefano Scialla, Strombeek-Bever (BE); Claudia Crestini, Rome (IT); Heiko Lange, Rome (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/189,009

(22) Filed: Jun. 22, 2016

(65) Prior Publication Data

US 2016/0375138 A1    Dec. 29, 2016

(30) Foreign Application Priority Data

Jun. 24, 2015    (EP) .................................... 15173590

(51) Int. Cl.
| | |
|---|---|
| *A61K 8/97* | (2017.01) |
| *A61K 47/30* | (2006.01) |
| *A61Q 5/02* | (2006.01) |
| *A61Q 5/12* | (2006.01) |
| *A61K 8/72* | (2006.01) |
| *A61Q 19/00* | (2006.01) |
| *C07G 1/00* | (2011.01) |
| *C08H 7/00* | (2011.01) |
| *C09G 1/00* | (2006.01) |
| *C11D 3/382* | (2006.01) |
| *C08L 97/00* | (2006.01) |
| *C11D 3/00* | (2006.01) |
| *C11D 17/06* | (2006.01) |

(52) U.S. Cl.
CPC ................ *A61K 47/30* (2013.01); *A61K 8/72* (2013.01); *A61Q 5/02* (2013.01); *A61Q 5/12* (2013.01); *A61Q 19/00* (2013.01); *C07G 1/00* (2013.01); *C08H 6/00* (2013.01); *C08L 97/005* (2013.01); *C09G 1/00* (2013.01); *C11D 3/0084* (2013.01); *C11D 3/382* (2013.01); *C11D 17/06* (2013.01)

(58) Field of Classification Search
None
See application file for complete search history.

(56) References Cited

U.S. PATENT DOCUMENTS

| | | | |
|---|---|---|---|
| 2,352,021 A | 6/1944 | Schubert et al. | |
| 3,912,706 A | 10/1975 | Rachor et al. | |
| 5,512,276 A | 4/1996 | Lang et al. | |
| 6,100,385 A | 8/2000 | Naae et al. | |
| 8,075,637 B2 | 12/2011 | Gizaw et al. | |
| 2003/0139319 A1 | 7/2003 | Scheibel | |
| 2003/0156970 A1 | 8/2003 | Oberkofler et al. | |
| 2008/0125544 A1 | 5/2008 | Yao | |
| 2010/0075878 A1* | 3/2010 | Gizaw ...................... | A61K 8/97 510/119 |
| 2011/0114539 A1 | 5/2011 | Stokes et al. | |
| 2013/0233037 A1 | 9/2013 | Adam | |
| 2016/0374921 A1 | 12/2016 | Massey-Brooker et al. | |
| 2016/0374922 A1 | 12/2016 | Massey-Brooker et al. | |
| 2016/0374928 A1 | 12/2016 | Massey-Brooker et al. | |
| 2016/0374935 A1 | 12/2016 | Massey-Brooker et al. | |
| 2016/0376408 A1 | 12/2016 | Massey-Brooker et al. | |

FOREIGN PATENT DOCUMENTS

| | | |
|---|---|---|
| CN | 104 147 977 A | 11/2014 |
| JP | S63 97612 A | 4/1988 |
| JP | H07 215988 A | 8/1995 |
| WO | WO 2010/135804 A1 | 12/2010 |

(Continued)

OTHER PUBLICATIONS

U.S. Appl. No. 15/189,005, filed Jun. 22, 2016, Massey-Brooker, et al.
U.S. Appl. No. 15/189,007, filed Jun. 22, 2016, Massey-Brooker, et al.
U.S. Appl. No. 15/189,011, filed Jun. 22, 2016, Massey-Brooker, et al.
U.S. Appl. No. 15/189,016, filed Jun. 22, 2016, Massey-Brooker, et al.
U.S. Appl. No. 15/189,019, filed Jun. 22, 2016, Massey-Brooker, et al.
Lora, Jairo H., et al., Recent Industrial Applications of Lignin: A Sustainable Alternative to Nonrenewable Materials, Journal of Polymers and the Environment, Apr. 2002, pp. 39-48, vol. 10, Nos. 112, XP-002493248.

(Continued)

*Primary Examiner* — Brian Gulledge
(74) *Attorney, Agent, or Firm* — John T. Dipre; Steven W. Miller

(57) ABSTRACT

The present invention relates to a consumer goods product comprising a consumer goods product ingredient and a functionalized lignin oligomer, wherein the functionalized lignin oligomer: (a) comprises less than 1 wt % sulphur content; (b) has a number average molecular weight ($\overline{M}_n$) of from 800 Da to 1,800 Da; and (c) comprises at least one functional group selected from carboxyl, ketone, aldehyde, amino and quaternary ammonium, wherein only one type of functional group selected from the group consisting of list is present at a level of at least 0.8 mmol/g, and wherein if any other functional group selected from the group consisting of list is present, it is present at a level of below 0.8 mmol/g, wherein the lignin oligomer is derived from corn, sugar cane, wheat and any combination thereof, and wherein the consumer goods product is selected from an oral care composition, an antiseptic cream, or a detergent composition.

9 Claims, No Drawings

(56) References Cited

FOREIGN PATENT DOCUMENTS

WO  WO 2010/135805 A1  12/2010
WO  WO 2014/178911 A1  11/2014

OTHER PUBLICATIONS

Pan, Xuejun, et al., Organosolv Ethanol Lignin from Hybrid Poplar as a Radical Scavenger: Relationship between Lignin Structure, Extraction Conditions, and Antioxidant Activity, J. Agric. Food Chem., 2006, pp. 5806-5813, vol. 54, XP008148495.
Ugartondo, Vanessa, et al., Comparative antioxidant and cytotoxic effects of lignins from different sources, Bioresource Technology, 2008, pp. 6683-6687, vol. 99.
Zhang, Jianfeng, et al., Reductive Degradation of Lignin and Model Compounds by Hydrosilanes, ACS Sustainable Chemistry & Engineering, 2014, pp. 1983-1991, vol. 2.
Uraki, Yasumitsu, et al., Novel Functions of Non-Ionic, Amphiphilic Lignin Derivatives In: ACS Symposium Series, Jan. 1, 2012, pp. 243-254, American Chemical Society/ Oxford University Press, vol. 1107, Chapter 13, XP055235971.
Extended European Search Report; Application No. 15173599.0-1460; dated Jan. 15, 2016, 9 pages.
Extended European Search Report; Application No. 15173603.0-1460; dated Jan. 15, 2016, 8 pages.
Database GNPD [Online], MINTEL, Mar. 2009, "Eye Contour Cream", XP002751692, Database accession No. 1102156.
Database GNPD [Online], MINTEL, Apr. 2012, "Aloe Vera Shower Gel", XP002751693, Database accession No. 1765683.

* cited by examiner

CONSUMER GOODS PRODUCT COMPRISING FUNCTIONALISED LIGNIN OLIGOMER

FIELD OF THE INVENTION

The present invention relates to consumer goods products comprising functionalized lignin oligomer.

BACKGROUND OF THE INVENTION

Lignins provide anti-oxidant benefits and can act as a surface deposition aid in consumer goods products, such as skin treatment compositions, hair treatment compositions, oral care compositions home care compositions and detergent compositions (especially hand wash detergents). In addition, for home care applications, lignins can also provide surface modification benefits which lead to improved shine and water repellence benefits.

However, lignins are difficult to incorporate in consumer goods products due to their poor solubility in water. In addition, many lignins, such as Kraft lignin, comprise sulphur, which leads to poor chemical compatibility with other ingredients that may be present in consumer goods products, such as transition metals. Sulphur may also cause malodour problems.

Multi-functionalisation of sulphur containing lignin is taught by U.S. Pat. No. 8,075,637. However, multi functionalisation of small lignin oligomer molecules can lead to a poor water-solubility. The inventors have found that specific functionalisation by a predominantly single type of functional group provides a lignin oligomer that exhibits good solubility in water. In addition, specific functionalisation by a predominantly single type of functional group can also enable a higher loading of the functional group onto the lignin oligomer. This is especially important because of the relatively low molecular weight of the lignin oligomer.

SUMMARY OF THE INVENTION

The present invention relates to a The present invention relates to a consumer goods product comprising a consumer goods product ingredient and a functionalised lignin oligomer, wherein the functionalised lignin oligomer: (a) comprises less than 1 wt % sulphur content; (b) has a number average molecular weight ($\overline{M}_n$) of from 800 Da to 1,800 Da; and (c) comprises at least one functional group selected from carboxyl, ketone, aldehyde, amino and quaternary ammonium, wherein only one type of functional group selected from this list is present at a level of at least 0.8 mmol/g, and wherein if any other functional group selected from this list is present, it is present at a level of below 0.8 mmol/g, wherein the lignin oligomer is derived from corn, sugar cane, wheat and any combination thereof, and wherein the consumer goods product is selected from an oral care composition, an antiseptic cream, or a detergent composition.

DETAILED DESCRIPTION OF THE INVENTION

Consumer Goods Product:

The consumer goods product comprises a consumer goods product ingredient and a functionalised lignin oligomer, wherein the functionalised lignin oligomer: (a) comprises less than 1 wt % sulphur content; (b) has a number average molecular weight ($\overline{M}_n$) of from 800 Da to 1,800 Da; and (c) comprises at least one functional group selected from carboxyl, ketone, aldehyde, amino and quaternary ammonium, wherein only one type of functional group selected from this list is present at a level of at least 0.8 mmol/g, and wherein if any other functional group selected from this list is present, it is present at a level of below 0.8 mmol/g.

The consumer goods product may comprise an emollient and/or humectant.

The consumer goods product may comprise an emulsifier, this may be especially preferred when the lignin oligomer is in the form of an emulsion.

The product may be an oral care composition.

The product may be an antiseptic cream.

The product may be a detergent composition.

The consumer goods product may comprise chitin and/or chitin derivative.

The consumer goods product is typically selected from: hard surface cleaning sheet and/or wipe; and teeth treatment strip.

The consumer goods product is typically selected from: handwash laundry detergent; handwash dishwashing detergent; soap bar; liquid handwash soap; and toothpaste.

Consumer Goods Product Ingredient:

Suitable consumer goods product ingredients include emmolient, humectants, emulsifiers, and any combination thereof.

Functionalised Lignin Oligomer:

The functionalised lignin oligomer: (a) comprises less than 1 wt % sulphur content; (b) has a number average molecular weight ($\overline{M}_n$) of from 800 Da to 1,800 Da; and (c) comprises at least one functional group selected from carboxyl, ketone, aldehyde, amino and quaternary ammonium, wherein only one type of functional group selected from this list is present at a level of at least 0.8 mmol/g, and wherein if any other functional group selected from this list is present, it is present at a level of below 0.8 mmol/g.

Preferably, the lignin oligomer has a weight average molecular weight ($\overline{M}_w$) in the range of from 800 Da to 5,000 Da.

Preferably, the lignin oligomer has a number average molecular weight ($\overline{M}_n$) in the range of from 800 Da to 1,200 Da.

Preferably, the lignin oligomer is essentially free of sulphur.

Preferably, the lignin oligomer has an ester content in the range of from 0.0 mmol/g to 0.1 mmol/g.

Preferably, the lignin oligomer is derived from corn, sugar cane, wheat and any combination thereof.

Functionalisation of Lignin:

Lignin (500 mg) is dissolved in water containing sodium hydroxide (amount corresponding to 1 equivalent (eq.) to total acidic groups in the lignin, i.e., phenolic hydroxyl and carboxylic acid groups). After 1 h of stirring, the suitably terminated functional, e.g., an epoxide-terminated functional, is added (depending on the desired technical loading in ranges from 0.25 to 10.0 eq. to lignin phenolic hydroxyl groups) and the reaction mixture is stirred at 50° C. overnight. In order to assure appropriate mixing of lignin and functional in the reaction mixture, additives such as emulsifiers, e.g., non-ionic surfactants, can be used.

After cooling to room temperature and acidifying to pH 2 using 10% (v/v) aqueous hydrogen chloride solution, the resulting suspension is centrifuged (15 min at 500 rpm) to recover the precipitated lignin. The functionalised lignin is then washed 3 times with 50 mL acidified water (pH 2) followed by renewed isolation via centrifugation (15 min at 500 rpm) each time. The final pellet was subsequently freeze-dried. The freeze-dried material is used for analysis and application without any additional manipulation.

How to Measure Functionalisation Content:

The determination of the technical loading of a given functionalised lignin with a given added functional is determined as follows: Ca. 30 mg of the functionalised lignin are accurately weighed in a volumetric flask and suspended in 400 μL of the above prepared solvent solution. One hundred microliters of the internal standard solution are added, followed by 100 μL of 2-chloro-4,4,5,5-tetramethyl-1,3,2-dioxaphospholane (Cl-TMDP). The flask is tightly closed, and the mixture is stirred for 120 min at ambient temperature. $^{31}$P NMR spectra are recorded using suitable equipment under the conditions reported above for the determination of aliphatic and aromatic hydroxyl contents. Quantitative analysis is done according to the procedure outlined above for the determination of aliphatic and aromatic hydroxyl contents.

Technical loadings are determined by comparing the abundancies of total aromatic hydroxyl groups of the product lignin with the starting lignin, corrected for background hydrolysis reactions.

Structural Aspects of Functionalised Lignin Oligomer:

It may be preferred for a structural motif (L) to connect the lignin backbone and the functional group, such as carboxylic group, ammonium group, or polyethylene glycol chain. Such L motif bonding is preferentially, but not exclusively, via reaction of activated hydroxyl groups directly being a part of the structural features making up the lignin backbone with reactive species carrying preferentially but not exclusively an epoxide functionality or a hydroxyl group on an aliphatic chain with a leaving group in α-position; this leaving group is preferentially, but not exclusively selected from the group of chloride, bromide, iodide, mesylate, triflate, tosylate.

Method of Measuring Sulphur Content:

The chemical composition of a lignin sample in terms of its carbon (C), hydrogen (H), nitrogen (N) and sulphur (S) content can be determined by elemental analysis in form of a CHNS analysis of at least three different representative samples of a given batch of the respective lignin. Typical sample sizes are 2.0 mg of a lignin sample that was oven-dried at 105° C. until a steady weight was obtained. The samples are placed in aluminum dishes and analyzed using a Carlo-Erba NA 1500 analyzer, using helium as carrier gas. Carbon (C), hydrogen (H), nitrogen (N) and sulphur (S) were detected in form of carbon dioxide, water, nitrogen, and sulphur dioxide, which are chromatographically separated to exit the instrument in the order of nitrogen, carbon dioxide, water, and sulphur dioxide. Quantification is achieved against calibrations using typical standard substances used for the calibration of elemental analysers, such as (bis(5-tert-butyl-2-benzo-oxazol-2-yl) thiophene, based on the peak areas of the chromatograms obtained for each lignin sample.

Method of Measuring $\overline{M}_n$ and $\overline{M}_w$:

The number average molecular weight, $\overline{M}_n$, as well as the weight average molecular weight, $\overline{M}_w$, can be determined using gel permeation chromatography (GPC). Prior to analysis, representative lignin samples are acetobrominated as reported in archival literature (J. Asikkala, T. Tamminen, D. S. Argyropoulos, J. Agric. Food Chem. 2012, 60, 8968-8973.) to ensure complete solubilisation in tetrahydrofuran (THF). 5 mg lignin is suspended in 1 mL glacial acetic acid/acetyl bromide (9:1 v/v) for 2 h. The solvent is then removed under reduced pressure, and the residue is dissolved in HPLC-grade THF and filtered over a 0.45 μm syringe filter prior to injection into a 20 μL sample loop. Typical analysis set-ups resemble the following specific example: GPC-analyses are performed using a Shimadzu instrument consisting of a controller unit (CBM-20A), a pumping unit (LC 20AT), a degasser unit (DGU-20A3), a column oven (CTO-20AC), a diode array detector (SPD-M20A), and a refractive index detector (RID-10A); the instrumental set-up is controlled using the Shimadzu Lab-Solution software package (Version 5.42 SP3). Three analytical GPC columns (each 7.5×30 mm) are connected in series for analyses: Agilent PLgel 5 μm 10000 Å, followed by Agilent PLgel 5 μm 1000 Å and Agilent PLgel 5 μm 500 Å. HPLC-grade THF (Chromasolv®, Sigma-Aldrich) is used as eluent (isocratic at 0.75 mL min-1, at 40° C.). Standard calibration is performed with polystyrene standards (Sigma Aldrich, MW range 162–5×106 g mol-1), and lower calibration limits are verified/adjusted by the use of synthesized dimeric and trimeric lignin models. Final analyses of each sample is performed using the intensities of the UV signal at λ=280 nm employing a tailor-made MS Excel-based table calculation, in which the number average molecular weight ($\overline{M}_n$) and the weight average molecular weight ($\overline{M}_w$) is calculated based on the measured absorption (in a.u.) at a given time (min) after corrections for baseline drift and THF-stemming artifacts.

$\overline{M}_n$ is calculated according to the formula $$\overline{M}_n = \frac{\sum w_i}{\sum \frac{w_i}{M_i}}$$

in which $\overline{M}_n$ is the number average molecular weight
$w_i$ is obtained via $$w_i = -h_i \frac{dV}{d(\log M)}$$

with M being molecular weight
hi being the signal intensity of a given log M measurement point
V being the volume of the curve over a given log M interval d(log M).
$M_i$ is a given molecular weight.
The analysis is run in triplicate, and final values are obtained as the standard average.

$\overline{M}_w$ is calculated according to the formula $$\overline{M}_w = \frac{\sum w_i M_i}{\sum w_i}$$

in which $\overline{M}_w$ is the number average molecular weight
$w_i$ is obtained via $$w_i = -h_i \frac{dV}{d(\log M)}$$

with M being the molecular weight
hi being the signal intensity of a given log M measurement point V being the volume of the curve over a given log M interval d(log M).

$M_i$ is a given molecular weight.

The analysis is run in triplicate, and final values are obtained as the standard average.

Eventually necessary adjustment of $\overline{M}_n$ and $\overline{M}_w$ with respect to the desired applications is achieved by mechanical breaking of polymeric lignin using a ball mill, by chemically or enzymatically polymerising oligomeric lignin.

Method of Measuring Aromatic Hydroxyl and Aliphatic Hydroxyl Content:

Typically, a procedure similar to the one originally published can be used (A. Granata, D. S. Argyropoulos, J. Agric. Food Chem. 1995, 43, 1538-1544). A solvent mixture of pyridine and (CDCl3) (1.6:1 v/v) is prepared under anhydrous conditions. The NMR solvent mixture is stored over molecular sieves (4 Å) under an argon atmosphere. Cholesterol is used as internal standard at a concentration of 0.1 mol/L in the aforementioned NMR solvent mixture. 50 mg of Cr(III) acetyl acetonate are added as relaxation agent to this standard solution.

Ca. 30 mg of the lignin are accurately weighed in a volumetric flask and suspended in 400 µL of the above prepared solvent solution. One hundred microliters of the internal standard solution are added, followed by 100 µL of 2-chloro-4,4,5,5-tetramethyl-1,3,2-dioxaphospholane (Cl-TMDP). The flask is tightly closed, and the mixture is stirred for 120 min at ambient temperature. 31P NMR spectra are recorded using suitable equipment, similar or identical to the following example: On a Bruker 300 MHz NMR spectrometer, the probe temperature is set to 20° C. To eliminate NOE effects, the inverse gated decoupling technique is used. Typical spectral parameters for quantitative studies are as follows: 90° pulse width and sweep width of 6600 Hz. The spectra are accumulated with a delay of 15 s between successive pulses. Line broadening of 4 Hz is applied, and a drift correction is performed prior to Fourier transform. Chemical shifts are expressed in parts per million from 85% H3PO4 as an external reference. All chemical shifts reported are relative to the reaction product of water with Cl-TMDP, which has been observed to give a sharp signal in pyridine/CDCl3 at 132.2 ppm. To obtain a good resolution of the spectra, a total of 256 scans are acquired. The maximum standard deviation of the reported data is 0.02 mmol/g, while the maximum standard error is 0.01 mmol/g. (A. Granata, D. S. Argyropoulos, J. Agric. Food Chem. 1995, 43, 1538-1544). Quantification on the basis of the signal areas at the characteristic shift regions (in ppm, as reported in A. Granata, D. S. Argyropoulos, J. Agric. Food Chem. 1995, 43, 1538-1544) is done using a tailor-made table calculation in which the abundances, given in mmol/g, of the different delineable phosphitylated hydroxyl groups are determined on the basis of the integral obtained for the signal of the internal standard, that is present in the analysis sample at a concentration of 0.1 m, creating a signal at the interval ranging from 144.5 ppm to 145.3 ppm. The area underneath the peak related to the internal standard is set to a value of 1.0 during peak integration within the standard processing of the crude NMR data, allowing for determining abundances using simple rule-of-proportion mathematics under consideration of the accurate weight of the sample used for this analysis. The analysis is run in triplicate, and final values are obtained as the standard average.

Method of Measuring Hydrolysable Ester Content:

The total ester content of the lignin can be determined by subjecting the lignin to alkaline hydrolysis conditions: Ca. 500 mg of lignin are dissolved in an excess of 1 M sodium hydroxide solution and heated to temperatures of above 70-80° C. for 12 h. The lignin is subsequently precipitated by acidifying the reaction mixture, isolated and freeze-dried.

Ca. 30 mg of the lignin are accurately weighed in a volumetric flask and suspended in 400 µL of the above prepared solvent solution. One hundred microliters of the internal standard solution are added, followed by 100 µL of 2-chloro-4,4,5,5-tetramethyl-1,3,2-dioxaphospholane (Cl-TMDP). The flask is tightly closed, and the mixture is stirred for 120 min at ambient temperature. $^{31}$P NMR spectra are recorded using suitable equipment under the conditions reported above for the determination of aliphatic and aromatic hydroxyl contents. Quantification of the acid content is done on the basis of the signal intensities at the characteristic shift regions (in ppm) using a tailor-made table calculation referring to the signal of the internal standard. Abundances are typically given in mmol/g. The ester content is obtained as the difference in the abundances of acid groups, aliphatic hydroxyl groups, and aromatic hydroxyl groups found in untreated vs. the lignin treated with sodium hydroxide as outlined above. The analysis is run in triplicate, and final values are obtained as the standard average.

Emollient:

Suitable emollients are silicon based emollients. Silicone-based emollients are organo-silicone based polymers with repeating siloxane (Si 0) units. Silicone-based emollients of the present invention are hydrophobic and exist in a wide range of molecular weights. They include linear, cyclic and crosslinked varieties. Silicone oils are generally chemically inert and usually have a high flash point. Due to their low surface tension, silicone oils are easily spreadable and have high surface activity. Examples of silicon oil include: Cyclomethicones, Dimethicones, Phenyl-modified silicones, Alkyl-modified silicones, Silicones resins, Silica. Other emollients useful in the present invention can be unsaturated esters or fatty esters. Examples of unsaturated esters or fatty esters of the present invention include: Caprylic Capric Triglycerides in combination with Bis-PEG/PPG-1 6/16 PEG/PPG-16/16 Dimethicone and C12-C15 Alkylbenzoate.

The basic reference of the evaluation of surface tension, polarity, viscosity and spreadability of emollient can be found under Dietz, T., Basic properties of cosmetic oils and their relevance to emulsion preparations. SOFW-Journal, July 1999, pages 1-7.

Humectant:

A humectant is a hygroscopic substance used to keep things moist. Typically, it is often a molecule with several hydrophilic groups, most often hydroxyl groups; however, amines and carboxyl groups, sometimes esterified, can be encountered as well (its affinity to form hydrogen bonds with molecules of water is the crucial trait). A humectant typically attracts and retains the moisture in the air nearby via absorption, drawing the water vapour into and/or beneath the organism/object's surface.

Suitable humectants include: Propylene glycol, hexylene glycol, and butylene glycol, Glyceryl triacetate, Neoagarobiose, Sugar alcohols (sugar polyols) such as glycerol, sorbitol, xylitol, maltitol, Polymeric polyols such as polydextrose, Quillaia, Urea, Aloe vera gel, MP diol, Alpha hydroxy acids such as lactic acid, Honey, Lithium chloride Emulsifier:

An emulsifier generally helps disperse and suspend a discontinuous phase within a continuous phase in an oil-in-water emulsion. A wide variety of conventional emulsifiers are suitable for use herein. Suitable emulsifiers include: hydrophobically-modified cross-linked polyacrylate polymers and copolymers, polyacrylamide polymers and copolymers, and polyacryloyldimethyl taurates. More preferred examples of the emulsifiers include: acrylates/C10-30 alkyl acrylate cross-polymer having tradenames Pemulen™ TR-1, Pemulen™ TR-2 (all available from Lubrizol); acrylates/ steareth-20 methacrylate copolymer with tradename ACRYSOL™ 22 (from Rohm and Hass); polyacrylamide with tradename SEPIGEL 305 (from Seppic).

EXAMPLES

Example 1

The following samples were evaluated by the method described below. Sample A is Lignin functionalised with carboxylic groups. Sample B is Lignin functionalised with quaternary ammonium groups. Sample C is Lignin functionalised with both carboxylic and quaternary ammonium groups. Samples A and B are the inventions examples and Sample C is the comparison example. All of samples A, B and C are derived from wheat.

Functionalisation Content of the Lignin Samples:

|  | Carboxy | Ketone | Aldehyde | Amino | Quaternary ammonium |
|---|---|---|---|---|---|
| Sample A (carboxy) | 1.7 | 0.2 | <0.1 | 0.0 | 0.0 |
| Sample B (quaternary ammonium) | 0.6 | 0.2 | <0.1 | <0.1 | 1.7 |
| Sample C (carboxy & quaternary ammonium) | 0.9 | 0.2 | <0.1 | <0.1 | 0.8 |

Other Properties of the Functionalized Lignin Oligomer Samples:

|  | Sulphur content | Number average molecular weight ($\overline{M}_n$) |
|---|---|---|
| Sample A (carboxy) | Less than 1% | 1000 Da-1200 Da |
| Sample B (quaternary ammonium) | Less than 1% | 1000 Da-1200 Da |
| Sample C (carboxy & quaternary ammonium) | Less than 1% | 1000 Da-1200 Da |

Process of Making the Samples:

Preparation of Turbidity Samples: Weigh out 0.1 g of functionalised lignin oligomer and disperse in 1 liter of non-ionic based hard surface cleaning product (Flash) water dispersion and stir it for 15 minutes at 200 rpm at room temperature. Then, measure the turbidity of the aqueous dispersion using the below method with Scanalys MPS-1 system Using sodium carbonate, pH was increased by one unit increments and turbidity was measured at pH 8.

Turbidity Data:

| Sample | Nephelometric Turbidity Units (NTU) |
|---|---|
| Sample A: carboxy functionalised lignin oligomer | 19 ± 1 |
| Sample B: quaternary ammonium functionalised lignin oligomer | 19 ± 1 |
| Sample C: carboxy & quaternary ammonium functionalised lignin oligomer | 59 ± 1 |

Sample A and B (in accordance with the present invention) has superior solubility profile than sample C.

Example 2, Illustrative Examples

Hand Dishwashing:

| Examples | Wt % New Product I | Wt % New Product II |
|---|---|---|
| Alkyl ethoxy sulfate AExS | 16 | 16 |
| Amine oxide | 5.0 | 5.0 |
| C9-11 EO8 | 5 | 5 |
| GLDA | 0.7 | 0.7 |
| Solvent | 1.3 | 1.3 |
| Polypropylene glycol (Mn = 2000) | 0.5 | 0.5 |
| Sodium chloride | 0.8 | 0.8 |
| Lignin | 0.01 | 1.0 |
| Water | Balance | Balance |

Granular Laundry Detergent Compositions Designed for Front-Loading Automatic Washing Machines:

|  | Wt % New Product | Wt % New Product |
|---|---|---|
| Linear alkylbenzenesulfonate | 8 | 8 |
| AE3S | 0 | 0 |
| C12-14 Alkylsulfate | 1 | 1 |
| AE7 | 2.2 | 2.2 |
| $C_{10-12}$ Dimethyl hydroxyethylammonium chloride | 0.75 | 0.75 |
| Crystalline layered silicate (δ-$Na_2Si_2O_5$) | 4.1 | 4.1 |
| Zeolite A | 5 | 5 |
| Citric Acid | 3 | 3 |
| Sodium Carbonate | 15 | 15 |
| Silicate 2R ($SiO_2:Na_2O$ at ratio 2:1) | 0.08 | 0.08 |
| Soil release agent | 0.75 | 0.75 |
| Acrylic Acid/Maleic Acid Copolymer | 1.1 | 1.1 |
| Carboxymethylcellulose | 0.15 | 0.15 |
| Protease - Purafect ® (84 mg active/g) | 0.2 | 0.2 |
| Amylase - Stainzyme Plus ® (20 mg active/g) | 0.2 | 0.2 |
| Lipase - Lipex ® (18.00 mg active/g) | 0.05 | 0.05 |
| Amylase - Natalase ® (8.65 mg active/g) | 0.1 | 0.1 |
| Cellulase - Celluclean ™ (15.6 mg active/g) | 0 | 0 |
| TAED | 3.6 | 3.6 |
| Percarbonate | 13 | 13 |
| Na salt of Ethylenediamine-N,N'-disuccinic acid, (S,S) isomer (EDDS) | 0.2 | 0.2 |
| Hydroxyethane di phosphonate (HEDP) | 0.2 | 0.2 |
| $MgSO_4$ | 0.42 | 0.42 |
| Perfume | 0.5 | 0.5 |
| Suds suppressor agglomerate | 0.05 | 0.05 |
| Soap | 0.45 | 0.45 |

-continued

|  | Wt %<br>New Product | Wt %<br>New Product |
| --- | --- | --- |
| Sulphonated zinc phthalocyanine (active) | 0.0007 | 0.0007 |
| S-ACMC | 0.01 | 0.01 |
| Direct Violet 9 (active) | 0 | 0 |
| Lignin | 0.01 | 1.0 |
| Sulfate/Water & Miscellaneous | Balance | Balance |

Automatic Dishwashing Cleaning Composition:

|  | Powder (wt % based on 19 g portion) | Powder (wt % based on 19 g portion) | Powder (wt % based on 19 g portion) |
| --- | --- | --- | --- |
| STPP | 34-38 | 34-38 | 34-38 |
| Alcosperse[1] | 7-12 | 7-12 | 7-12 |
| SLF-18 Polytergent[2] | 1-2 | 1-2 | 1-2 |
| Esterified substituted benzene sulfonate[3] | 0.1-6.0 | 0.1-6.0 | 0.1-6.0 |
| Polymer[4] | 0.2-6.0 | 0.2-6.0 | 0.2-6.0 |
| Sodium perborate monohydrate | 2-6 | 2-6 | 2-6 |
| Carbonate | 20-30 | 20-30 | 20-30 |
| 2.0r silicate | 5-9 | 5-9 | 5-9 |
| Sodium disilicate | 0-3 | 0-3 | 0-3 |
| Enzyme system[5] | 0.1-5.0 | 0.1-5.0 | 0.1-5.0 |
| Pentaamine cobalt(III)chloride dichloride salt | 10-15 | 10-15 | 10-15 |
| TAED | 0-3 | 0-3 | 0-3 |
| Perfume, dyes, water and other components | Balance to 100% | Balance to 100% | Balance to 100% |

|  | Liquid (wt % based on 1.9 g portion) | Liquid (wt % based on 1.9 g portion) | Liquid (wt % based on 1.9 g portion) |
| --- | --- | --- | --- |
| Dipropylene Glycol | 35-45 | 35-45 | 35-45 |
| SLF-19 Polytergent[2] | 40-50 | 40-50 | 40-50 |
| Neodol ® C11EO9 | 1-3 | 1-3 | 1-3 |
| Lignin | 0.05 | 0.01 | 1.0 |
| Dyes, water and other components | Balance | Balance | Balance |

[1] such as Alcosperse ® 246 or 247, a sulfonated copolymer of acrylic acid from Alco Chemical Co.
[2] linear alcohol ethoxylate from Olin Corporation
[3] such as those described above
[4] a sulfonated polymer such as those described above
[5] one or more enzymes such as protease, mannaway, natalase, lipase and mixture thereof The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A consumer goods product comprising a consumer goods product ingredient and a functionalised lignin oligomer,
    wherein the functionalised lignin oligomer
    (a) comprises less than about 1 wt % sulphur content;
    (b) has a number average molecular weight ($\overline{M}_n$) of from about 800 Da to about 1,800 Da; and
    (c) comprises at least one functional group selected from carboxyl, ketone, aldehyde, amino and quaternary ammonium,
    wherein only one type of functional group selected from the group consisting of list is present at a level of at least about 0.8 mmol/g,
    and wherein if any other functional group selected from the group consisting of list is present, it is present at a level of below about 0.8 mmol/g,
    wherein the lignin oligomer is derived from corn, sugar cane, wheat and any combination thereof,
    and wherein the consumer goods product is a detergent composition, wherein functional group is a carboxyl.

2. A consumer goods product according to claim 1, wherein if any other functional group selected from the list is present, it is present at a level of below about 0.6 mmol/g.

3. A consumer goods product according to claim 1, wherein only one type of functional group selected from the list is present at a level of at least about 0.9 mmol/g.

4. A consumer goods product according to claim 1, wherein the lignin oligomer has a weight average molecular weight ($\overline{M}_w$) in the range of from about 800 Da to about 5,000 Da.

5. A consumer goods product according to claim 1, wherein the lignin oligomer has a number average molecular weight ($\overline{M}_n$) in the range of from about 800 Da to about 1,200 Da.

6. A consumer goods product according to claim 1, wherein the lignin oligomer has a hydrolysable ester content in the range of from about 0.0 mmol/g to about 0.7 mmol/g.

7. A consumer goods product according to claim 1, wherein the consumer goods product comprises an emollient and/or humectant.

8. A consumer goods product according to claim 1, wherein the consumer goods product comprises an emulsifier, and wherein the lignin oligomer is in the form of an emulsion.

9. A consumer goods product according to claim 1, wherein the consumer goods product comprises chitin and/or chitin derivatives.

* * * * *